United States Patent [19]

Yamamoto et al.

[11] Patent Number: 4,668,277
[45] Date of Patent: May 26, 1987

[54] PYRAZOLESULFONYLUREA USEFUL FOR CONTROLLING THE GROWTH OF UNDESIRED VEGETATION

[75] Inventors: Susumu Yamamoto; Toshiaki Sato, both of Funabashi; Takasi Ikai, Tokyo; Tosihiko Oguti; Tsutomu Nawamaki, both of Yono, all of Japan

[73] Assignee: Nissan Chemical Industries, Ltd., Tokyo, Japan

[21] Appl. No.: 713,430

[22] Filed: Mar. 19, 1985

[30] Foreign Application Priority Data

Mar. 22, 1984 [JP] Japan .................................. 59-55126

[51] Int. Cl.$^4$ .................... A01N 43/48; C07D 239/02
[52] U.S. Cl. ............................................. 71/92; 544/320
[58] Field of Search ............................. 544/320; 71/92

[56] References Cited

FOREIGN PATENT DOCUMENTS

| 87780 | 9/1983 | European Pat. Off. . | |
|---|---|---|---|
| 96003 | 12/1983 | European Pat. Off. . | |
| 95925 | 12/1983 | European Pat. Off. . | |
| 148879 | 9/1983 | Japan . | |
| 13778 | 1/1984 | Japan ................................. | 544/320 |
| 31775 | 2/1984 | Japan . | |
| 122488 | 7/1984 | Japan . | |
| 199686 | 11/1984 | Japan . | |
| 219281 | 12/1984 | Japan ................................. | 544/320 |
| 28975 | 2/1985 | Japan . | |
| 45573 | 3/1985 | Japan . | |
| 45574 | 3/1985 | Japan ................................. | 544/320 |
| 78981 | 5/1985 | Japan ................................. | 544/320 |
| 78980 | 5/1985 | Japan . | |
| 3850 | 5/1983 | South Africa . | |

OTHER PUBLICATIONS

Boehner et al, Chem. Abst., 100-156641d.

Primary Examiner—Donald G. Daus
Assistant Examiner—Cecilia Shen
Attorney, Agent, or Firm—Frishauf, Holtz, Goodman & Woodward

[57] ABSTRACT

There are disclosed a compound formula (I):

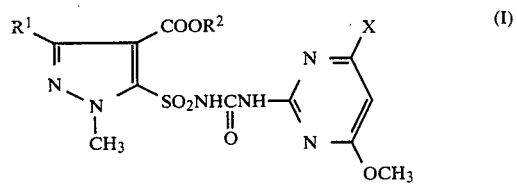

wherein $R^1$ represents a chlorine atom or a bromine atom; $R^2$ represents methyl or ethyl; and X represents methyl or methoxy; a herbicidal composition containing the same as an active ingredient; and a method of use of the compound represented by formula (I) for controlling the growth of weeds without harm to crop plants in the same location.

15 Claims, No Drawings

PYRAZOLESULFONYLUREA USEFUL FOR CONTROLLING THE GROWTH OF UNDESIRED VEGETATION

This invention relates to a novel pyrazolesulfonylurea derivative represented by the formula (I), a herbicide containing said derivative as an active ingredient and a herbicidal method for use thereof.

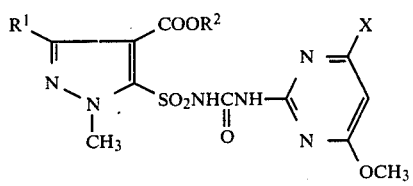

wherein $R^1$ represents a chlorine atom or a bromine atom; $R^2$ represents methyl or ethyl; and X represents methyl or methoxy.

In order to protect such important crops as rice, wheat and corn from damage caused by various weeds to increase the yield of crops, it is indispensable to employ a herbicide. In particular, there has recently been desired a selective herbicide capable of selectively killing weeds without exhibiting any phytotoxicity to crops even when the herbicide is used to treat simultaneously the stem-leaf portions of both the crops and the weeds in a cultivated field where such crops and weeds coexist.

From the viewpoint of the prevention of environmental pollution, the reduction of economical cost for transportation, spraying, and so on, a herbicide which exhibits high herbicidal effect even at low concentration, has been sought. While some compounds having such a property have presently been used as selective herbicides, there still exists a demand for a novel compound having such a property.

The present inventors have continued for many years to research the herbicidal properties of many compounds to find a selective compound having high weed-killing ability and to develop a herbicide having high selectivity to weeds. The present inventors have found that the compound of the present invention represented by the above general formula (I) exhibits strong herbicidal effect against many weeds when it is employed either for soil treatment or for stem-leaf treatment and has low phytotoxicity to such important crops as rice, wheat and corn, and accomplished the present invention.

Further, the compound according to the present invention exhibits higher herbicidal activity with much smaller amount thereof as compared with conventional herbicides, and hence is also useful as a herbicide for orchard and non-cultivated fields.

The prior art relating to the present invention, for example, European Patent Publication No. 87780 discloses a general formula which is generic to the compound of the present invention. However, the compound of the present invention is not disclosed therein.

The compound of the present invention exhibits much lower phytotoxicity to the rice plant, while maintaining high herbicidal activity against weeds, as compared with the compounds disclosed specifically in the prior art.

It is extremely important and advantageous to reduce phytotoxicity to rice plants of a herbicide, and it is the characteristic feature of the present invention to have reduced the practical danger of such phytotoxicity.

As seen from the Test examples shown below, the compound according to the present invention can be applied effectively to the direct seeded culture where phytotoxicity has been assumed to appear more easily.

Therefore, the present invention enables the spread of even the direct seeded culture which has not been spread due to the danger of phytotoxicity, and hence is very important in agriculture.

The compound of the present invention shows as well extremely low phytotoxicity against corn and wheat, and exhibits also high herbicidal effect against velvet leaf and yellow nutsedge which have been assumed to be difficult to be prevented or controlled.

Typical examples of the derivatives represented by the above formula (I) suitable for use as herbicides include those shown in Table 1 set forth below.

The Compounds Nos. in this Table are referred to in the following description.

TABLE 1

| Comp. No. | $R^1$ | $R^2$ | X | m.p. (°C.) |
|---|---|---|---|---|
| 1 | Cl | $CH_3$ | $CH_3$ | 187–188 |
| 2 | Cl | $CH_3$ | $OCH_3$ | 172–173 |
| 3 | Cl | $C_2H_5$ | $CH_3$ | 180–181 |
| 4 | Cl | $C_2H_5$ | $OCH_3$ | 169–170 |
| 5 | Br | $C_2H_5$ | $CH_3$ | 181–183 |
| 6 | Br | $C_2H_5$ | $OCH_3$ | 170–172 |

The compounds of this invention represented by the above formula (I) can readily be produced by selecting suitably the following reaction scheme 1 or 2.

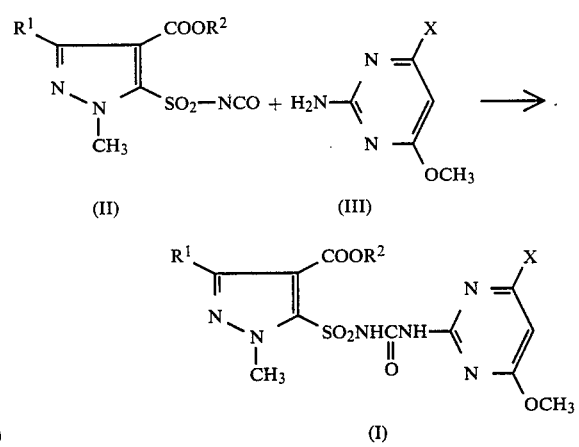

Reaction scheme 1 wherein $R^1$, $R^2$, and X have the same meanings as defined above.

That is, a pyrazolesulfonyl isocyanate derivative (II) is dissolved in an inert solvent such as sufficiently dried dioxane, acetonitrile, etc., and to the resultant solution is added a pyrimidine derivative (III). By stirring the mixture, the reaction proceeds generally rapidly to give the compound (I) of this invention. When the reaction proceeds difficultly, a minute amount of a suitable base such as triethylamine, triethylenediamine, pyridine, sodium ethoxide, sodium hydride, etc. may be added to the reaction mixture, whereby the reaction can proceed easily.

Reaction scheme 2:

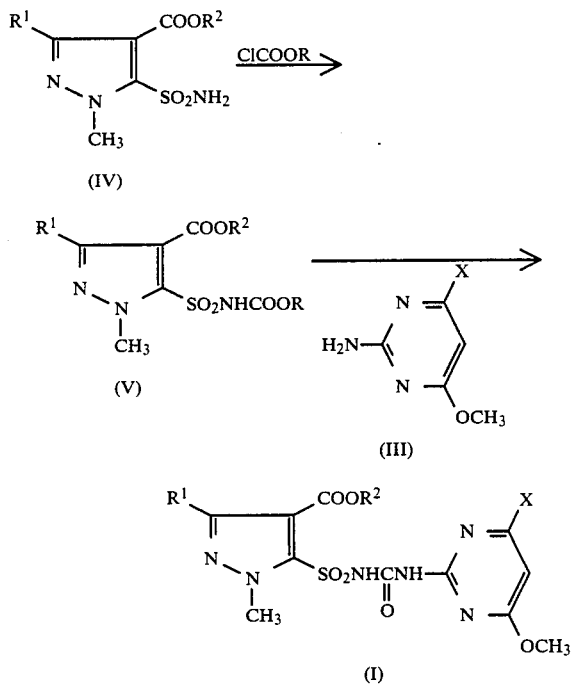

wherein $R^1$, $R^2$ and X have the same meanings as defined above, and R represents an alkyl group or a phenyl group.

That is, a pyrazolesulfonamide derivative (IV) is allowed to react with a chlorocarbonate in a solvent such as acetone or methyl ethyl ketone in the presence of a base such as potassium carbonate, followed by acid precipitation with hydrochloric acid, etc., to give a compound (V). This compound is then heated in a solvent such as toluene with a compound (III) to give the compound (I) to this invention.

Most of the pyrazolesulfonyl isocyanate derivatives are unstable in the air, and should preferably be stored in a cold and dark place under a nitrogen atmosphere when they are to be stored, but alternatively they can be used as such without purification in many cases in the subsequent reaction step.

Most of the intermediates pyrazolesulfonamides (IV) to be used in this invention are novel compounds, and synthetic examples thereof are shown below as Reference examples.

REFERENCE EXAMPLE 1

Synthesis of 3-chloro-4-ethoxycarbonyl-1-methylpyrazole-5-sulfonamide (1) Synthesis of ethyl 3-chloro-1-methylpyrazole-4-carboxylate:

Into a solution of 150 ml of conc. HCl, 50 ml of phosphoric acid (85%), 41.4 g of ethyl 3-amino-1-methylpyrazole-4-carboxylate and 100 ml of water, there was added dropwise a 50 ml of aqueous solution of 18.6 g of sodium nitrite at 0° C. or lower. The reaction mixture was added dropwise into a solution of 90 g of cupric sulfate (pentahydrate) and 60 g of sodium chloride dissolved in 200 ml of water at room temperature.

The mixture was heated for an hour at 50° C. and after cooling, followed by extraction with chloroform. After washing with water and drying, evaporation of the solvent gave 44.8 g of ethyl 3-chloro-1-methylpyrazole-4-carboxylate. m.p.: 65°-66° C.

(2) Synthesis of 3-chloro-4-ethoxycarbonyl-1-methylpyrazole-5-sulfonamide:

5.0 g of ethyl 3-chloro-1-methylpyrazole-4-carboxylate was dispersed in dry diethyl ether under cooling at −60° C. or lower. Into this solution there was added lithium diisopropylamide (1.2 molar equivalent) and after stirring for an hour sulfur dioxide gas was passed into this solution for 30 minutes. After stirring at −60° C. for 2 hours the reaction mixture was stirred at room temperature for 2 hours. Filtration and drying of the precipitate gave 6.0 g of lithium 3-chloro-4-ethoxycarbonyl-1-methlpyrazole-5-sulfinate. This product was added into a solution of 100 ml of ice-water and 100 ml of dichloromethane and 6.0 g of N-chloro succinimide was added thereinto at 0°-5° C. After stirring for 45 minutes at room temperature the dichloromethane layer was separated and water layer was extracted with 100 ml of dichloromethane. The combined dichloromethane solution of 3-chloro-4-ethoxycarbonyl-1-methylpyrazole-5-sulfonyl chloride (b.p.: 133° C./0.25 mmHg.) was added dropwise into 80 ml of aqueous ammonia (28%) under cooling at 10° C. After stirring for an hour, evaporation of the solvent gave 3.6 g of 3-chloro-4-ethoxycarbonyl-1-methylpyrazole-5-sulfonamide.

m.p.: 121°-123° C.

REFERENCE EXAMPLE 2

Synthesis of 3-chloro-4-methoxycarbonyl-1-methylpyrazole-5-sulfonamide

Following the procedure as described in Reference example 1, 3-chloro-4-methoxycarbonyl-1-methylpyrazole-5-sulfonamide was synthesized. m.p.: 125°-126° C.

Intermediate compound: 3-chloro-4-methoxycarbonyl-1-methylpyrazole-5-sulfonyl chloride. b.p.: 123° C./0.25 mmHg.

REFERENCE EXAMPLE 3

Synthesis of 3-bromo-4-ethoxycarbonyl-1-methlpyrazole-5-sulfonamide

Following the procedure as described in Reference example 1, 3-bromo-4-ethoxycarbonyl-1-methylpyrazole-5-sulfonamide was synthesized. m.p.: 96°-98° C.

Specific synthetic examples of the compounds according to this invention are illustrated below by using the substituted pyrazolesulfonamides (IV) obtained in Reference examples, but this invention is not limited thereto.

EXAMPLE 1

Synthesis of
N-[(4,6-dimethoxypyrimidin-2-yl)aminocarbonyl]-3-chloro-4-ethoxycarbonyl-1-methylpyrazole-5-sulfonamide To a mixture of 7.0 g of 3-chloro-4-ethoxycarbonyl-1-methylpyrazole-5-sulfonamide, obtained in Reference example 1, 5.3 g of anhydrous potassium carbonate and 50 ml of dry acetone there was added 2.8 g of n-butyl isocyanate at room temperature, and the mixture was refluxed for 3 hours. After the reaction, acetone was evaporated under reduced pressure and the residue was dissolved in ice-water. After separation of a trace of water insolubles, the filtrate was made acidic with hydrochloric acid and the crystals formed were filtered, washed with water and dried to give 5.2 g of N-(n-butylcarbamoyl)-3-chloro-4-ethoxycarbonyl-1-methlpyrazole-5-sulfonamide. m.p.: 109°–111° C.

Into a mixture of 120 ml of dry toluene and the product obtained from the above procedure, under reflux, 4.2 g of phosgene was passed. Then, the reaction mixture was further refluxed for 1.5 hours. After completion of the reaction, evaporation under reduced pressure gave crude 3-chloro-4-ethoxycarbonyl-1-methyl-pyrazole-5-sulfonyl isocyanate.

The crude isocyanate was taken out in an amount of 0.98 g, and added into 20 ml of dry acetonitrile solution of 400 mg of 2-amino-4,6-dimethoxypyrimidine. The mixture was stirred at romm temperature and the crystals precipitated were filtered, washed and dried to give 0.8 g of N-[(4,6-dimethoxypyrimidin-2-yl)aminocarbonyl]-3-chloro-4-ethoxycarbonyl-1-methylpyrazole-5-sulfonamide.

m.p.: 169°–170° C.

EXAMPLE 2

Synthesis of
N-[(4-methoxy-6-methylpyrimidin-2-yl)aminocarbonyl]-3-chloro-4-ethoxycarbonyl-1-methylpyrazole-5-sulfonamide Into 30 ml of dry acetone, there were added 5.35 g of 3-chloro-4-ethoxycarbonyl-1-methylpyrazole-5-sulfonamide, 2.5 g of ethyl chloroformate and 4.14 g of anhydrous potassium carbonate and the mixture was refluxed for three hours. After cooling, acetone was evaporated and the residue was added into ice-water. After separation of a trace of water insolubles, the filtrate was made acidic with hydrochloric acid. The reaction mixture was extrated with diethyl ether and organic layer was dried and the solvent was evaporated under reduced pressure to give 6.0 g of N-(ethoxycarbonyl)-3-chloro-4-ethoxycarbonyl-1-methylpyrazole-5-sulfonamide.

m.p.: 82°–85° C.

Into 20 ml of toluene, 2.8 g of N-(ethoxycarbonyl)-3-chloro-4-ethoxycarbonyl-1-methlpyrazole-5-sulfonamide obtained in the above process and 1.4 g of 2-amino-4-methoxy-6-methylpyrimidine were added. After reflux for 8 hours and some portion of toluene was distilled off, then the crystal of the title compound was obtained.

m.p.: 180°–181° C.

In the above process, N-(methoxycarbonyl)-3-chloro-4-ethoxycarbonyl-1-methylpyrazole-5-sulfonamide (m.p. 107°–110° C.), which was obtained by using methyl chloroformate instead of ethyl chloroformate, could be used to obtain the title compound.

In application of the compounds of this invention as herbicides, they can be applied by mixing with solid carriers, including for example clay, talc, bentonite, diatomaceous earth and others or liquid carriers, including for example water, alcohols (methanol, ethanol and the like), aromatic hydrocarbons (benzene, toluene, xylene and the like), chlorinated hydrocarbons, ethers, ketones, esters (ethyl acetate, etc.), acid amides and others. They can be provided for practical use with addition of any desired additive selected from an emulsifier, a dispersing agent, a suspending agent, a wetting agent, a spreader and a stabilizer and in any desired form such as a soluble concentrate, an emulsifiable concentrate, a wettable powder, a dust, a granule, a suspension concentrate, etc.

In the following, there are shown examples of formulations of herbicides containing the compounds of this invention as active ingredients, but they are not limitative of this invention. In the exemplary formulations shown below, "parts" means "parts by weight".

| Exemplary formulation 1: Wettable powder | |
|---|---|
| Compound No. 1 of this invention | 50 parts |
| Ziegleit A | 46 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

All of the above components are mixed and pulverized homogeneously to prepare a wettable powder. In use, the above wettable powder is diluted with water to 50 to 50,000 times, and sprayed in an amount of the active ingredient of 0.0005 kg to 10 kg per hectare.

| Exemplary formulation 2: Wettable powder | |
|---|---|
| Compound No. 2 of this invention | 75 parts |
| Ziegleit A | 19 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 4 parts |
| (white carbon; trade name, produced by Shionogi Seiyaku Co., Ltd.) | |

The above components are mixed and pulverized homogeneously to prepare a wettable powder.

| Exemplary formulation 3: Wettable powder | |
|---|---|
| Compound No. 3 of this invention | 50 parts |
| Ziegleit A | 46 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi | |

Exemplary formulation 3: Wettable powder

Seiyaku Co., Ltd.)

The above components are mixed and pulverized homogeneously to prepare a wettable powder.

Exemplary formulation 4: Wettable powder

| | |
|---|---|
| Compound No. 4 of this invention | 50 parts |
| Ziegleit A | 46 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder

Exemplary formulation 5: Wettable powder

| | |
|---|---|
| Compound No. 5 of this invention | 25 parts |
| Ziegleit A | 71 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 6: Wettable powder

| | |
|---|---|
| Compound No. 6 of this invention | 50 parts |
| Ziegleit A | 44 parts |
| (kaolin type clay: produced by Ziegleit Kogyo Co., Ltd.) | |
| Solpol 5039 | 4 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 7: Emulsifiable concentrate

| | |
|---|---|
| Compound No. 2 of this invention | 2 parts |
| Xylene | 78 parts |
| Dimethylformamide | 15 parts |
| Solpol 2680 | 5 parts |
| (mixture of nonionic surfactant and anionic surfactant; trade name; produced by Toho Kagaku Co., Ltd.) | |

The above components are homogeneously mixed to prepare an emulsifiable concentrate. In use, the above emulsifiable concentrate is diluted to 10 to 10,000 times and sprayed in an amount of the active ingredient of 0.0005 to 10 kg per hectare.

Exemplary formulation 8: Suspension concentrate

| | |
|---|---|
| Compound No. 4 of this invention | 25 parts |
| Agrisol S-710 | 10 parts |
| (nonionic surfactant; trade name; produced by Kao-Atlas Co., Ltd.) | |
| Runox 1000 C | 0.5 part |
| (anionic surfactant; trade name; produced by Toho Kagaku Co., Ltd.) | |
| 1% Rodopol water | 20 parts |
| (thickener; trade name; produced by Rohne Poulainc) | |

The above components are mixed to provide a suspension concentrate preparation.

Exemplary formulation 9: Granule

| | |
|---|---|
| Compound No. 1 of this invention | 0.1 parts |
| Bentonite | 55 parts |
| Talc | 44.9 parts |

All of the above components are mixed and pulverized homogeneously, then a little amount of water is added and the while is stirred, kneaded and granulated by excluding granulator, then dried to prepare a granule.

Exemplary formulation 10: Granule

| | |
|---|---|
| Compound No. 2 of this invention | 0.25 parts |
| Bentonite | 55 parts |
| Talc | 44.57 parts |

All of the above components are mixed and pulverized homogenerously, then a little amount of water is added and the whole is stirred, kneaded and granulated by excluding granulator, then dried to prepare a granule.

Exemplary formulation 11: Granule

| | |
|---|---|
| Compound No. 4 of this invention | 0.5 parts |
| Bentonite | 55 parts |
| Talc | 44.5 parts |

All of the above components are mixed and pulverized homogeneously, when a little amount of water is added and the whole is stirred, kneaded and granulated by excluding granulator, then dried to prepare a granule.

Exemplary formulation 12: Granule

| | |
|---|---|
| Compound No. 6 of this invention | 1 part |
| Bentonite | 55 parts |
| Talc | 44 parts |

All of the above components are mixed and pulverized homogeneously, then a little amount of water is added and the whole is stirred, kneaded and granulated by excluding granulator, then dried to prepare a granule.

If desired, the compound of this invention can be applied as a mixture with other kinds of herbicides, various insecticides, sterilizers or adjuvants during preparation or spraying.

As the other kinds of herbicides as mentioned above, there may be included those as described in Farm Chemicals Handbook, 69th edition (1983).

The compounds of this invention can also be applied, in addition to the agricultural and horticultural fields such as farm fields, paddy fields, fruit gardens and the like, to athletic grounds, vacant lands, belts along the railroads and others. The amounts of the pesticide to be applied, which may differ depending on the scenes to be applied, the time of application, the application method, the kinds of the objective grasses and the crops harvested, may generally range suitably from 0.005 to 10 kg per hectare.

The following test examples are set forth for illustration of the utility of the compounds of this invention as herbicides.

TEST EXAMPLE 1

Herbicidal effect test by soil treatment

In a plastic box of 15 cm in length, 22 cm in width and 6 cm in depth, there was placed a deluvium soil, seeds of (A) rice (*Oryza sativa*), (B) barnyardgrass (*Echinochloa crusgalli*), (D) annual sedge (*Cyperus microiria*), (E) lambsquarters (*Chenopodium ficifolium*), (F) common purslane (*Portulaca oleracea*), (G) hairly galinosoga (*Galinosoga ciliata*), and (H) yellow cress (*Rorippa atrovirens*) were sown mixedly. After covering soil to about 1.5 cm over the seeds, herbicides were sprayed evenly on the soil surface to predetermined proportions of the active ingredient. In spraying, the wettable powder as shown in the foregoing exemplary formulations was diluted with water and sprayed over the entire surface by means of a small sprayer. Four weeks after spraying, the herbicidal effect on rice and the various weeds were examined according to the judgement criteria shown below. The results are shown in Table 2.

| Judgement criteria: |
| --- |
| 5 ... Growth control rates of more than 90% (almost completely withered) |
| 4 ... Growth control rates of 70 to 90% |
| 3 ... Growth control rates of 40 to 70% |
| 2 ... Growth control rates of 20 to 40% |
| 1 ... Growth control rates of 5 to 20% |
| 0 ... Growth control rates of less than 5% (substantially no effect) |

The above growth control rates are determined by measuring the top fresh weights of the treated plants and those of the non-treated plants, and calculated from the following formula:

$$\text{Growth control rate (\%)} = 1 - \frac{\text{Top fresh weight of the treated plants}}{\text{Top fresh weight of the non-treated plants}} \times 100$$

TABLE 2

| Comp. No. | Amount of active ingredient applied (Kg/ha) | (A) | (B) | (D) | (E) | (F) | (G) | (H) |
| --- | --- | --- | --- | --- | --- | --- | --- | --- |
| 1 | 0.16 | 1 | 5 | 5 | 5 | 5 | 5 | 5 |
|   | 0.08 | 0 | 4 | 5 | 5 | 5 | 5 | 5 |
| 2 | 0.16 | 1 | 5 | 5 | 5 | 5 | 5 | 5 |
|   | 0.08 | 1 | 4 | 5 | 5 | 5 | 5 | 5 |
| 3 | 0.16 | 1 | 5 | 5 | 5 | 5 | 5 | 5 |
|   | 0.08 | 0 | 4 | 5 | 5 | 5 | 5 | 5 |
| 4 | 0.16 | 2 | 5 | 5 | 5 | 5 | 5 | 5 |
|   | 0.08 | 1 | 4 | 5 | 5 | 5 | 5 | 5 |
| 5 | 0.16 | 0 | 5 | 5 | 5 | 5 | 5 | 5 |
|   | 0.08 | 0 | 4 | 5 | 5 | 5 | 5 | 5 |
| 6 | 0.16 | 0 | 4 | 5 | 5 | 5 | 5 | 5 |
|   | 0.08 | 0 | 3 | 5 | 5 | 5 | 5 | 5 |
| control A | 0.16 | 5 | 5 | 5 | 5 | 5 | 5 | 5 |
|   | 0.08 | 5 | 5 | 5 | 5 | 5 | 5 | 5 |
| control B | 0.16 | 5 | 5 | 5 | 5 | 5 | 5 | 5 |
|   | 0.08 | 5 | 5 | 5 | 4 | 5 | 5 | 5 |
| control C | 0.16 | 5 | 5 | 5 | 5 | 5 | 5 | 5 |
|   | 0.08 | 5 | 5 | 5 | 5 | 5 | 5 | 5 |
| control D | 0.16 | 4 | 5 | 5 | 5 | 5 | 5 | 5 |
|   | 0.08 | 4 | 4 | 5 | 5 | 5 | 5 | 5 |
| control E | 0.16 | 5 | 5 | 5 | 5 | 5 | 5 | 5 |
|   | 0.08 | 5 | 4 | 5 | 5 | 5 | 5 | 5 |
| control F | 0.16 | 5 | 5 | 5 | 5 | 5 | 5 | 5 |
|   | 0.08 | 5 | 5 | 5 | 5 | 5 | 5 | 5 |
|   | 0.32 | 4 | 1 | 3 | 3 | 1 | 3 | 4 |
| G | 0.16 | 3 | 0 | 2 | 2 | 0 | 2 | 3 |
| control | 0.32 | 4 | 4 | 3 | 4 | 5 | 5 | 3 |
| H | 0.16 | 3 | 3 | 2 | 3 | 4 | 4 | 2 |
| control I | 0.16 | 5 | 5 | 5 | 5 | 5 | 5 | 5 |
|   | 0.08 | 5 | 5 | 5 | 5 | 5 | 5 | 5 |

Control Compounds in the above Table 2 are as follows:

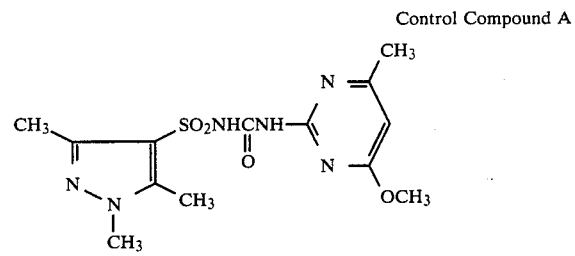

Control Compound A

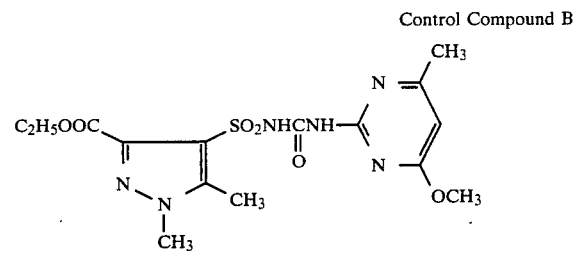

Control Compound B

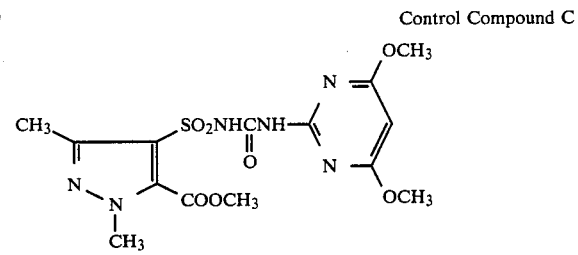

Control Compound C

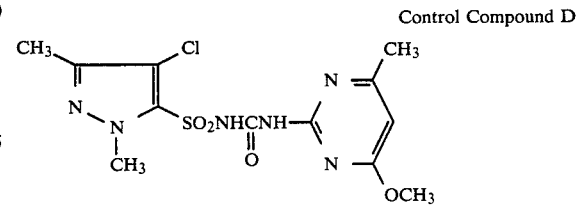

Control Compound D

Control Compound E

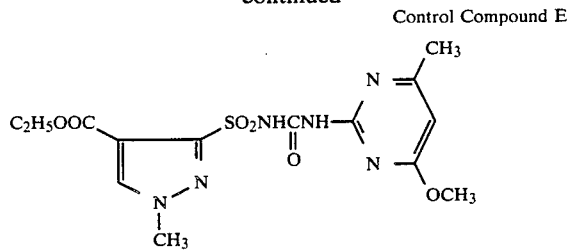

Control Compound F

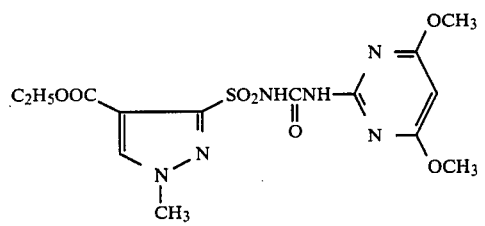

Control Compound G

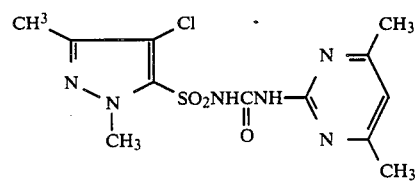

Control Compound H

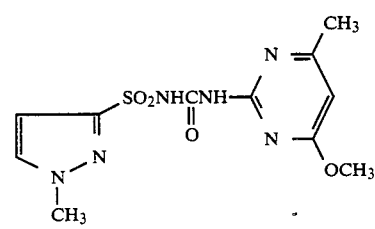

Control Compound I

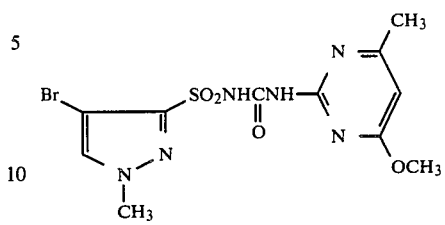

TEST EXAMPLE 2

Herbicidal effect test by stem-leaf treatment

In a plastic box of 15 cm in length, 22 cm in width and 6 cm in depth, there was placed a deluvium soil, seeds of (A) rice (*Oryza sativa*), (D) annual sedge (*Cyperus microiria*), (E) lambsquarters (*Chenopodium ficifolium*), (F) common purslane (*Portulaca oleracea*), (G) hairly galinosoga (*Galinosoga ciliata*), (H) yellow cress (*Rorippa atrovirens*), (I) corn (*Zea mays*), (K) wheat (*Triticum vulgare*), and (L) tomato (*Lycopersicum esculentum*) were sown in shapes of spots, respectively, followed by covering of soil to about 1.5 cm over the seeds. After respective plants have grown to the second and the third leaf stage, herbicides were sprayed evenly onto the stem-leaf portion at predetermined proportions of the active ingredient.

In spraying, the wettable powder as shown in the foregoing exemplary formulations was diluted with water and sprayed over the entire surface of the stem-leaf portions of various weeds by means of a small sprayer.

Four weeks after spraying, the herbicidal effect on rice and the various plants were examined according to the judgement criteria as shown in Test example 1. The results are shown in Table 3.

TABLE 3

| Comp. No. | Amount of active ingredient applied (Kg/ha) | (A) | (D) | (E) | (F) | (G) | (H) | (I) | (K) | (L) |
|---|---|---|---|---|---|---|---|---|---|---|
| 1 | 0.16 | 0 | 5 | 5 | 5 | 5 | 5 | 1 | 1 | 0 |
|   | 0.08 | 0 | 5 | 5 | 5 | 5 | 5 | 0 | 0 | 0 |
| 2 | 0.16 | 0 | 5 | 5 | 5 | 5 | 5 | 0 | 0 | 0 |
|   | 0.08 | 0 | 5 | 5 | 5 | 5 | 5 | 0 | 0 | 0 |
| 3 | 0.16 | 2 | 5 | 5 | 5 | 5 | 5 | 2 | 0 | 0 |
|   | 0.08 | 0 | 5 | 5 | 5 | 5 | 5 | 0 | 0 | 0 |
| 4 | 0.16 | 0 | 5 | 5 | 5 | 5 | 5 | 0 | 0 | 1 |
|   | 0.08 | 0 | 5 | 5 | 5 | 5 | 5 | 0 | 0 | 0 |
| 5 | 0.16 | 0 | 5 | 5 | 5 | 5 | 5 | 2 | 1 | 1 |
|   | 0.08 | 0 | 5 | 5 | 5 | 5 | 5 | 1 | 0 | 0 |
| 6 | 0.16 | 0 | 5 | 5 | 5 | 5 | 5 | 1 | 0 | 0 |
|   | 0.08 | 0 | 5 | 5 | 5 | 5 | 5 | 0 | 0 | 0 |
| control A | 0.16 | 5 | 5 | 5 | 5 | 5 | 5 | 5 | 4 | 2 |
|   | 0.08 | 5 | 5 | 5 | 5 | 5 | 5 | 5 | 3 | 1 |
| Control B | 0.32 | 5 | 4 | 3 | 3 | 3 | 4 | 5 | 4 | 3 |
|   | 0.16 | 4 | 3 | 2 | 2 | 2 | 3 | 4 | 3 | 2 |
| Control C | 0.16 | 5 | 5 | 5 | 5 | 5 | 5 | 5 | 5 | 5 |
|   | 0.08 | 5 | 5 | 5 | 5 | 5 | 5 | 5 | 5 | 5 |
| Control D | 0.16 | 4 | 5 | 4 | 5 | 4 | 5 | 4 | 4 | 1 |
|   | 0.08 | 4 | 4 | 4 | 5 | 4 | 4 | 4 | 3 | 1 |
| Control E | 0.16 | 5 | 4 | 4 | 4 | 3 | 5 | 4 | 5 | 1 |
|   | 0.08 | 5 | 4 | 4 | 4 | 3 | 4 | 4 | 4 | 1 |
| Control F | 0.16 | 5 | 5 | 5 | 5 | 5 | 4 | 5 | 5 | 2 |
|   | 0.08 | 5 | 5 | 5 | 5 | 5 | 4 | 5 | 5 | 1 |
| Control G | 0.32 | 4 | 3 | 2 | 3 | 3 | 4 | 2 | 2 | 1 |
|   | 0.16 | 3 | 2 | 1 | 2 | 2 | 3 | 1 | 1 | 0 |
| Control H | 0.32 | 5 | 5 | 4 | 4 | 4 | 5 | 5 | 5 | 4 |
|   | 0.16 | 5 | 3 | 3 | 3 | 2 | 3 | 5 | 5 | 3 |
| Control I | 0.16 | 5 | 5 | 5 | 5 | 5 | 5 | 5 | 5 | 5 |

TABLE 3-continued

| Comp. No. | Amount of active ingredient applied (Kg/ha) | (A) | (D) | (E) | (F) | (G) | (H) | (I) | (K) | (L) |
|---|---|---|---|---|---|---|---|---|---|---|
| I | 0.08 | 4 | 5 | 5 | 5 | 5 | 5 | 5 | 5 | 5 |

The control compounds A–I are the same as those in the foregoing Test example 1.

TEST EXAMPLE 3

Herbicidal effect test under paddy condtion

In a Wagner pot of 1/50 m², there was placed an alluvial soil, water was put thereinto, soil and water were mingled and a paddy condition of 2 cm depth of the water was made. Seeds of (B) barnyardgrass (*Echinochloa crusgalli*), (M) ducksalad (*Monochoria vaginalis*), (N) false pimpernel (*Lindernia procumbens*), (O) toothcup (*Rotala indica*) and (P) bulrush (*Scirpus hotarui*) were sown mixedly therein and tuberns of (Q) arrowhead (*Sagittaria pygmaea*), (R) perennial flat sedge (*Cyperus serotinus*) and (S) water chestnut (*Eleocharis kuroguwai*) were placed thereon. Then, young rice plants of the 2.5 leaf stage were transplanted.

On the next day, the diluted solution containing the compound of this invention was dropped on the water surface in predetermined proportions of the active ingredient.

Three weeks after application, the herbicidal effect on rice and the various weeds were examined according to the judgement criteria as shown in Test example 1. The results are shown in Table 4.

TABLE 4

| Comp. No. | Amount of active ingredient applied (Kg/ha) | (A) | (B) | (M) | (N) | (O) | (P) | (Q) | (R) | (S) |
|---|---|---|---|---|---|---|---|---|---|---|
| 1 | 0.32 | 1 | 5 | 5 | 5 | 5 | 5 | 5 | 5 | 5 |
|   | 0.16 | 0 | 5 | 5 | 5 | 5 | 5 | 5 | 5 | 5 |
|   | 0.08 | 0 | 5 | 5 | 5 | 5 | 5 | 5 | 5 | 5 |
|   | 0.04 | 0 | 5 | 5 | 5 | 5 | 5 | 5 | 5 | 5 |
| 2 | 0.32 | 1 | 5 | 5 | 5 | 5 | 5 | 5 | 5 | 5 |
|   | 0.16 | 0 | 5 | 5 | 5 | 5 | 5 | 5 | 5 | 5 |
|   | 0.08 | 0 | 5 | 5 | 5 | 5 | 5 | 5 | 5 | 5 |
|   | 0.04 | 0 | 5 | 5 | 5 | 5 | 5 | 5 | 5 | 5 |
| 3 | 0.32 | 0 | 5 | 5 | 5 | 5 | 5 | 5 | 5 | 5 |
|   | 0.16 | 0 | 5 | 5 | 5 | 5 | 5 | 5 | 5 | 5 |
|   | 0.08 | 0 | 5 | 5 | 5 | 5 | 5 | 5 | 5 | 5 |
|   | 0.04 | 0 | 5 | 5 | 5 | 5 | 5 | 5 | 5 | 5 |
| 4 | 0.32 | 0 | 5 | 5 | 5 | 5 | 5 | 5 | 5 | 5 |
|   | 0.16 | 0 | 5 | 5 | 5 | 5 | 5 | 5 | 5 | 5 |
|   | 0.08 | 0 | 5 | 5 | 5 | 5 | 5 | 5 | 5 | 5 |
|   | 0.04 | 0 | 5 | 5 | 5 | 5 | 5 | 5 | 5 | 5 |
| 5 | 0.32 | 0 | 5 | 5 | 5 | 5 | 5 | 5 | 5 | 5 |
|   | 0.16 | 0 | 5 | 5 | 5 | 5 | 5 | 5 | 5 | 5 |
|   | 0.08 | 0 | 5 | 5 | 5 | 5 | 5 | 5 | 5 | 5 |
|   | 0.04 | 0 | 5 | 5 | 5 | 5 | 5 | 5 | 5 | 5 |
| 6 | 0.32 | 0 | 5 | 5 | 5 | 5 | 5 | 5 | 5 | 5 |
|   | 0.16 | 0 | 5 | 5 | 5 | 5 | 5 | 5 | 5 | 5 |
|   | 0.08 | 0 | 5 | 5 | 5 | 5 | 5 | 5 | 5 | 5 |
|   | 0.04 | 0 | 5 | 5 | 5 | 5 | 5 | 5 | 5 | 5 |
| Control A | 0.32 | 5 | 5 | 5 | 5 | 5 | 5 | 5 | 5 | 5 |
|   | 0.16 | 5 | 5 | 5 | 5 | 5 | 5 | 5 | 5 | 5 |
|   | 0.08 | 5 | 5 | 5 | 5 | 5 | 5 | 5 | 5 | 5 |
|   | 0.04 | 5 | 5 | 5 | 5 | 5 | 5 | 5 | 5 | 5 |
| Control C | 0.32 | 5 | 5 | 5 | 5 | 5 | 5 | 5 | 5 | 5 |
|   | 0.16 | 5 | 5 | 5 | 5 | 5 | 5 | 5 | 5 | 5 |
|   | 0.08 | 5 | 5 | 5 | 5 | 5 | 5 | 5 | 5 | 5 |
|   | 0.04 | 5 | 5 | 5 | 5 | 5 | 5 | 5 | 5 | 5 |
| Control F | 0.32 | 5 | 5 | 5 | 5 | 5 | 5 | 5 | 5 | 5 |
|   | 0.16 | 5 | 5 | 5 | 5 | 5 | 5 | 5 | 5 | 5 |
|   | 0.08 | 5 | 5 | 5 | 5 | 5 | 5 | 5 | 5 | 5 |
|   | 0.04 | 5 | 5 | 5 | 5 | 5 | 5 | 5 | 5 | 5 |
| Control I | 0.32 | 5 | 5 | 5 | 5 | 5 | 5 | 5 | 5 | 5 |
|   | 0.16 | 5 | 5 | 5 | 5 | 5 | 5 | 5 | 5 | 5 |
|   | 0.08 | 5 | 5 | 5 | 5 | 5 | 5 | 5 | 5 | 5 |
|   | 0.04 | 5 | 5 | 5 | 5 | 5 | 5 | 5 | 5 | 5 |
| Control J | 0.32 | 4 | 5 | 5 | 5 | 5 | 5 | 5 | 5 | 5 |
|   | 0.16 | 3 | 5 | 5 | 5 | 5 | 5 | 5 | 5 | 5 |
|   | 0.08 | 2 | 5 | 5 | 5 | 5 | 5 | 5 | 5 | 5 |
|   | 0.04 | 0 | 5 | 5 | 5 | 5 | 5 | 5 | 5 | 5 |
| Control K | 0.32 | 4 | 5 | 5 | 5 | 5 | 5 | 5 | 5 | 5 |
|   | 0.16 | 3 | 5 | 5 | 5 | 5 | 5 | 5 | 5 | 5 |
|   | 0.08 | 2 | 5 | 5 | 5 | 5 | 5 | 5 | 5 | 5 |
|   | 0.04 | 0 | 5 | 5 | 5 | 5 | 5 | 5 | 5 | 5 |
| Control L | 0.32 | 4 | 5 | 5 | 5 | 5 | 5 | 5 | 5 | 5 |
|   | 0.16 | 3 | 5 | 5 | 5 | 5 | 5 | 5 | 5 | 5 |
|   | 0.08 | 2 | 5 | 5 | 5 | 5 | 5 | 5 | 5 | 5 |
|   | 0.04 | 0 | 5 | 5 | 5 | 5 | 5 | 5 | 5 | 5 |
| Control M | 0.32 | 4 | 5 | 5 | 5 | 5 | 5 | 5 | 5 | 5 |
|   | 0.16 | 3 | 5 | 5 | 5 | 5 | 5 | 5 | 5 | 5 |

TABLE 4-continued

| Comp. No. | Amount of active ingredient applied (Kg/ha) | (A) | (B) | (M) | (N) | (O) | (P) | (Q) | (R) | (S) |
|---|---|---|---|---|---|---|---|---|---|---|
| | 0.08 | 2 | 5 | 5 | 5 | 5 | 5 | 5 | 5 | 5 |
| | 0.04 | 0 | 5 | 5 | 5 | 5 | 5 | 5 | 5 | 5 |

TEST EXAMPLE 4

Herbicidal effect test and phytotoxicity test under the conditions of direct seeded rice culture After an alluvial soil was placed in a Wagner pot of 1/5000 are, water was added thereto and mixed with the soil to provide a submerged culture condition of a water-depth of 2 cm.

Pre-germinated rice seeds having a pigeon-breast shape were coated with a calcium oxide coating agent (tradename: Calper) and then sown in the soil at a depth of 1 cm.

Next day, a diluted formulation containing each of the compounds shown in table 5 was added with a pipette to the water-surface in the pot until a predetermined concentration of the compound was attained.

Four weeks after the dropwise addition of the diluted formulation, its phytotoxicity against rice plant was examined addording to the judgement criteria in Test example 1.

The results are shown in Table 5.

TABLE 5

| Comp. No. | Amount of active ingredient applied (Kg/ha) | Phyto-toxicity against rice plant | Comp. No. | Amount of active ingredient applied (Kg/ha) | Phytotoxi-ty against rice plant |
|---|---|---|---|---|---|
| 1 | 0.32 | 1 | 2 | 0.32 | 1 |
|   | 0.16 | 0 |   | 0.16 | 0 |
| 3 | 0.32 | 0 | 4 | 0.32 | 0 |
|   | 0.16 | 0 |   | 0.16 | 0 |
| 5 | 0.32 | 0 | 6 | 0.32 | 0 |
|   | 0.16 | 0 |   | 0.16 | 0 |
| J | 0.32 | 5 | K | 0.32 | 5 |
|   | 0.16 | 4 |   | 0.16 | 4 |
|   | 0.08 | 3 |   | 0.08 | 3 |
| L | 0.32 | 5 | M | 0.32 | 4 |
|   | 0.16 | 4 |   | 0.16 | 4 |
|   | 0.08 | 3 |   | 0.08 | 3 |

Control Compounds J–M in the above Tables 4 and 5 are as follows:

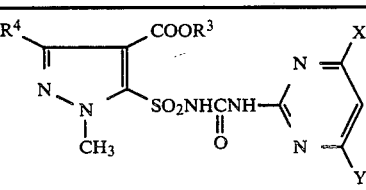

| Control | $R^3$ | $R^4$ | X | Y |
|---|---|---|---|---|
| J | $CH_3$ | H | $OCH_3$ | $OCH_3$ |
| K | $C_2H_5$ | H | $CH_3$ | $OCH_3$ |
| L | $CH_3$ | $CH_3$ | $CH_3$ | $CH_3$ |
| M | $CH_3$ | $CH_3$ | $OCH_3$ | $OCH_3$ |

TEST EXAMPLE 5

Effect test and test for phytotoxicity against cultivated plants—1

In a plastic box of 15 cm in length, 22 cm in width and 6 cm in depth, there was placed a sterilized diluvial soil, and seeds of (I) corn (Zea mays), (T) smart weed, (Polygonum longisetum), (U) cocklebur(Xanthium strumarium), (V) velvet leaf (Abutilon theophrasti) and (W) morning glory (Ipomoea Purpurea) were sown in shapes of spots, respectively. Further, a tuber of yellow nutsedge (Cyperus esculentus) was planted, respectively, followed by covering of soil to about 1.5 cm over the seeds.

When the corn reached the three leaf stage or when the weed reached the 1-2 leaf development stage, each of the active ingredients shown in Table 6 below was sprayed uniformly to the stem-leaf portions of various weeds in a predetermined amount of the ingredient.

The results are shown in Table 6.

TABLE 6

| Comp. No. | Amount of active ingredient applied (Kg/ha) | (I) | (T) | (U) | (V) | (W) | (X) |
|---|---|---|---|---|---|---|---|
| 1 | 0.10 | 0 | 5 | 5 | 5 | 5 | 5 |
|   | 0.05 | 0 | 5 | 5 | 5 | 5 | 5 |
| 2 | 0.10 | 0 | 5 | 5 | 5 | 5 | 5 |
|   | 0.05 | 0 | 5 | 5 | 5 | 5 | 5 |
| 3 | 0.10 | 0 | 5 | 5 | 5 | 5 | 5 |
|   | 0.05 | 0 | 5 | 5 | 5 | 5 | 5 |
| 4 | 0.10 | 0 | 5 | 5 | 5 | 5 | 5 |
|   | 0.05 | 0 | 5 | 5 | 5 | 5 | 5 |
| 5 | 0.10 | 0 | 5 | 5 | 5 | 5 | 5 |
|   | 0.05 | 0 | 5 | 5 | 5 | 5 | 5 |
| 6 | 0.10 | 0 | 5 | 5 | 5 | 5 | 5 |
|   | 0.05 | 0 | 5 | 5 | 5 | 5 | 5 |
| Atrazine | 0.5 | 0 | 5 | 2 | 1 | 5 | 0 |
| A | 0.05 | 5 | 5 | 5 | 5 | 5 | 5 |
| C | 0.05 | 5 | 5 | 5 | 5 | 5 | 5 |
| F | 0.05 | 5 | 5 | 5 | 5 | 5 | 5 |
| I | 0.05 | 5 | 5 | 5 | 5 | 5 | 5 |
| J | 0.05 | 5 | 5 | 5 | 5 | 5 | 5 |
| K | 0.05 | 5 | 5 | 5 | 5 | 5 | 5 |
| L | 0.05 | 5 | 5 | 5 | 5 | 5 | 5 |
| M | 0.05 | 5 | 5 | 5 | 5 | 5 | 5 |

TEST EXAMPLE 6

Effect test and test for phytotoxicity against cultivated plants—2

In a plastic box of 15 cm in length, 22 cm in width and 6 cm in depth, there was placed a sterilized diluvial soil, and then seeds of (K) wheat (Triticum vulgare), (Y) chickweed (Stellaria media), (Z) cleaver (Galium aparine) and (AA) wild mustard (Bassica Kaber) were sown in shapes of spots, respectively, followed by covering to about 1.5 cm over the seeds.

When the wheat reached the three leaf stage or when the weeds reached the 1-2 leaf development stage, each of the active ingredients was sprayed uniformly to the stem-leaf portion of the plants in a predetermined amount of the ingredient, respectively.

TABLE 7

| Comp. No. | Amount of active ingredient applied (Kg/ha) | (K) | (Y) | (Z) | (AA) |
| --- | --- | --- | --- | --- | --- |
| 1 | 0.10 | 0 | 5 | 5 | 5 |
|   | 0.05 | 0 | 5 | 5 | 5 |
| 2 | 0.10 | 0 | 5 | 5 | 5 |
|   | 0.05 | 0 | 5 | 5 | 5 |
| 3 | 0.10 | 0 | 5 | 5 | 5 |
|   | 0.05 | 0 | 5 | 5 | 5 |
| 4 | 0.10 | 0 | 5 | 5 | 5 |
|   | 0.05 | 0 | 5 | 5 | 5 |
| 5 | 0.10 | 0 | 5 | 5 | 5 |
|   | 0.05 | 0 | 5 | 5 | 5 |
| 6 | 0.10 | 0 | 5 | 5 | 5 |
|   | 0.05 | 0 | 5 | 5 | 5 |
| control C | 0.16 | 5 | 5 | 5 | 5 |
|   | 0.08 | 5 | 5 | 5 | 5 |
| Control E | 0.16 | 5 | 5 | 5 | 5 |
|   | 0.08 | 5 | 5 | 5 | 5 |
| Control F | 0.16 | 5 | 5 | 5 | 5 |
|   | 0.08 | 5 | 5 | 5 | 5 |
| Control I | 0.16 | 5 | 5 | 5 | 5 |
|   | 0.08 | 5 | 5 | 5 | 5 |

We claim:

1. A compound of the formula:

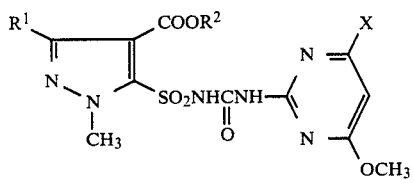

wherein $R^1$ represents a chlorine atom or a bromine atom; $R^2$ represents methyl or ethyl; and X represents methyl or methoxy.

2. A herbicidal composition which comprises an effective amount of a compound defined in claim 1 as an active ingredient together with a herbicidal carrier.

3. A method for controlling the growth of undesired vegetation which comprises applying to the locus to be protected an effective amount of a compound of claim 1.

4. The compound of claim 1 which is N-[(4-methoxy-6-methylpyrimidin-2-yl)aminocarbonyl]-3-chloro-4-methoxycarbonyl-1-methylpyrazole-5-sulfonamide.

5. The compound of claim 1 which is N-[(4,6-dimethoxypyrimidin-2-yl)aminocarbonyl]-3-chloro-4-methoxycarbonyl-1-methylpyrazole-5-sulfonamide.

6. The compound of claim 1 which is N-[(4-methoxy-6-methylpyrimidin-2-yl)aminocarbonyl]-3-chloro-4-ethoxycarbonyl-1-methylpyrazole-5-sulfonamide.

7. The compound of claim 1 which is N-[(4,6-dimethoxypyrimidin-2-yl)aminocarbonyl]-3-chloro-4-ethoxycarbonyl-1-methylpyrazole-5-sulfonamide.

8. The compound of claim 1 which is N-[(4-methoxy-6-methylpyrimidin-2-yl)aminocarbonyl]-3-bromo-4-ethoxycarbonyl-1-methylpyrazole-5-sulfonamide.

9. The compound of claim 1 which is N-[(4,6-dimethoxypyrimidin-2-yl)aminocarbonyl]-3-bromo-4-ethoxycarbonyl-1-methylpyrazole-5-sulfonamide.

10. The method for controlling the growth of undesired vegetation which comprises applying to the locus to be protected an effective amount of a compound of claim 4.

11. The method for controlling the growth of undesired vegetation which comprises applying to the locus to be protected an effective amount of a compound of claim 5.

12. The method for controlling the growth of undesired vegetation which comprises applying to the locus to be protected an effective amount of a compound of claim 6.

13. The method for controlling the growth of undesired vegetation which comprises applying to the locus to be protected an effective amount of a compound of claim 7.

14. The method for controlling the growth of undesired vegegation which comprises applying to the locus to be protected an effective amount of a compound of claim 8.

15. The method for controlling the growth of undesired vegetation which comprises applying to the locus to be protected an effective amount of a compound of claim 9.

* * * * *